(12) United States Patent
Balland Longeau et al.

(10) Patent No.: US 8,637,620 B2
(45) Date of Patent: Jan. 28, 2014

(54) METHOD FOR PREPARING POLYMER MATERIALS DOPED WITH METAL ELEMENTS AND RESULTING MATERIALS

(75) Inventors: Alexia Balland Longeau, Tours-France (FR); Louis Moreau, Pressigny (FR); Jérôme Thibonnet, Veigne (FR); Emilie Velasquez, Chambery (FR)

(73) Assignee: Commissariat A l'Energie Atomique et aux Energies Alternatives, Paris (FR)

( * ) Notice: Subject to any disclaimer, the term of this patent is extended or adjusted under 35 U.S.C. 154(b) by 686 days.

(21) Appl. No.: 12/682,024

(22) PCT Filed: Oct. 7, 2008

(86) PCT No.: PCT/EP2008/063389
§ 371 (c)(1),
(2), (4) Date: Sep. 10, 2010

(87) PCT Pub. No.: WO2009/047245
PCT Pub. Date: Apr. 16, 2009

(65) Prior Publication Data
US 2011/0137000 A1 Jun. 9, 2011

(30) Foreign Application Priority Data
Oct. 8, 2007 (FR) ..................... 07 58126

(51) Int. Cl.
*C08F 30/04* (2006.01)
*C07F 19/00* (2006.01)

(52) U.S. Cl.
USPC ............... 526/241; 560/38; 540/474; 534/16; 562/443

(58) Field of Classification Search
USPC ............... 526/241; 560/38; 540/474; 534/16; 562/443
See application file for complete search history.

(56) References Cited

U.S. PATENT DOCUMENTS 4,261,937 A    4/1981   Rinde

FOREIGN PATENT DOCUMENTS

EP      1 308 481 A2      7/2003
WO    WO 2007/120999 A2   10/2007

OTHER PUBLICATIONS

Faith et al., "Characterisation of Gold Particles of Various Size Distributions in Low Density Foams for Radiation Transport Experiments", Fusion Science and Technology, vol. 45, dated Mar. 2004, pp. 90-94.
David-Quillot et al., "A Novel Access to Organogermanium Compounds", Tetrahedron Letters, vol. 41 (2000), pp. 4905-4907.
Kawamura et al., "Cu(II)-assisted Helicity Induction on a Poly(phenylacetylene) Derivative Bearing and Achiral Glycine Residue with Amino Acids in Water", Chemistry Letters, vol. 32, No. 11 (2003) pp. 1086-1087.
Baxter et al., "Reductive Aminations of Carbonyl Compounds with Borohydride and Borane Reducing Agents," XP-002517937, Database accession No. 2008:1383655 CAPLUS, (John Wiley & Sons, Inc., 2002), pp. 1-40.

*Primary Examiner* — Robert D. Harlan
(74) *Attorney, Agent, or Firm* — Miles & Stockbridge P.C.

(57) ABSTRACT

The invention relates to a process for preparing a polymeric material doped with metal elements, comprising a step of polymerization of at least one monomer comprising at least one ethylenic function, said monomer being complexed with a metal element.

Use of the materials obtained by means of this process as catalysts, or luminescent or magnetic materials, or as elements for laser targets.

27 Claims, No Drawings

METHOD FOR PREPARING POLYMER MATERIALS DOPED WITH METAL ELEMENTS AND RESULTING MATERIALS

TECHNICAL FIELD

The present invention relates to a process for preparing polymeric materials doped with metal elements, to the polymeric materials that can be obtained by means of this process, to novel monomers and also to various uses of these polymeric materials.

These polymeric materials find their application in the overall field of applications appropriate for polymeric materials doped with metal elements, such as supported catalysis, luminescent materials, magnetic materials or ion-imprinteded materials. In particular, they find their application in the production of laser targets used in inertial confinement fusion experiments.

PRIOR ART

With regard to the extremely vast field of application of materials of this type, many teams have directed their research towards processes for producing such materials.

A first strategy has consisted in impregnating polymeric materials with metal salt solutions.

Thus, Rinde et al., in U.S. Pat. No. 4,261,937, describes a method for preparing polymer foams doped with a metal element, consisting in pouring a polymer gel into an aqueous solution comprising a salt of said metal element. The gel is then brought into contact with a series of solvents of decreasing polarity, in order to remove the water introduced. Each solvent used must be capable of solubilizing the previous solvent and is saturated with the chosen metal salt.

However, this method has the major drawback that the distribution of the metal element cannot be completely homogeneous at the atomic level, since crystallization of metal salts occurs during drying, followed by the formation of nanocrystals or microcrystals in the material. Furthermore, owing to the fact that the impregnation is carried out on a polymer gel, diffusion of the metal elements does not occur throughout the entire gel.

A second strategy consists, not in impregnating polymeric materials with a metal salt solution, but in doping materials of this type using solid metal particles.

Thus, Faith et al., in Fusion Science and Technology, Vol. 45, March 2004, p. 90-94, describe a process for preparing foams charged with solid gold particles, these foams being prepared by in situ polymerization in the presence of said particles of the trimethylolpropanetriacrylate monomer. However, this process does not enable homogeneous distribution within the material, the doping being in the form of aggregated particles comprising several tens or even hundreds of atoms.

Finally, a more recent strategy has consisted in preparing polymeric materials by copolymerization of organometallic monomers i.e. monomers of which the metal element is covalently bonded to one or more atoms of the monomer (as described in Tetrahedron Letters, 2000, 41, 4905).

However, this type of strategy can prove to be difficult to implement, since it requires the development of a chemistry specific to each metal that may be used as doping metal element.

Thus, there is a real need for a process for preparing polymeric materials doped with a metal element, which allows homogeneous incorporation of said metal element into the material and which does not require the development of a chemistry specific to the metal element to be incorporated.

DESCRIPTION OF THE INVENTION

To do this, the inventors have set out, judiciously, a process for preparing a polymeric material doped with a metal element, which combines both polymerization technology and coordination chemistry technology.

Thus, the invention relates, in general, to a process for preparing a polymeric material doped with at least one metal element, comprising a step of polymerization of a coordination complex of said metal element formed from said element and from one or more ligands of said element, said ligand(s) belonging to at least one monomer comprising at least one ethylenic group.

It is specified that, for the purpose of the invention, the term "coordination complex" is intended to mean a polyatomic structure comprising the doping metal element, around which groups belonging to at least one monomer are bound by coordination bonds, the coordination bond being created by introduction of a doublet of electrons belonging to said groups into an empty orbital of the metal element.

The process of the invention thus has the following advantages:

it allows the incorporation, into polymeric materials, of a broad diversity of metal elements, owing to the fact that the bonding between the metal elements and the monomer(s) occurs by coordination bonding;

it allows distribution of the metal element on the atomic scale;

it allows incorporation of high degrees of metal element, said degree depending on the amount of coordination complex used during the polymerization step.

According to the invention, the monomers comprising groups capable of constituting ligands are monomers comprising at least one group bearing a free doublet, in particular an amine group, and optionally at least one negatively charged group, in particular a carboxylate group. Advantageous monomers may comprise both at least one amine group and at least one carboxylate group, it being possible for these two types of groups to originate from an amino acid residue.

More specifically, monomers that can be used in the process of the invention and can form coordination complexes can correspond to formula (I) below:

in which:

R represents a group chosen from the groups of formulae below:

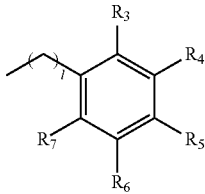 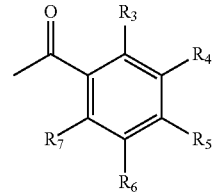

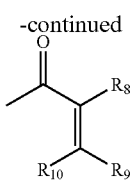

$R_1$ and $R_2$ represent, independently, H, an alkyl group, an aryl group, a group having the formulae below:

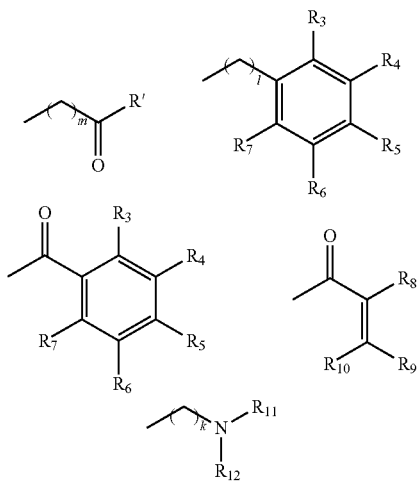

$R_{11}$ and $R_{12}$ corresponding, independently, to groups corresponding to the same definition as $R_1$ and $R_2$ given above;

R' is an $OR_{13}$ or amine group;

$R_3$, $R_4$, $R_5$, $R_6$ and $R_7$ represent, independently, H, an ethylenic group, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated into said groups, with the proviso that at least one of $R_3$, $R_4$, $R_5$, $R_6$ and $R_7$ represents an ethylenic group;

$R_8$, $R_9$ and $R_{10}$ represent, independently, H, an ethylenic group, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated in said groups;

$R_{13}$ represents H, a metal, such as an alkali metal, an alkyl group, an aryl group, an acyl group or an alkylaryl group, said alkyl, aryl and alkylaryl groups being optionally perfluorinated, and it being possible for one or more oxygen, sulphur and/or selenium atoms to be intercalated in said groups;

k, l and m are integers ranging from 0 to 20;

and the salts thereof.

Before going into greater detail in the description of the abovementioned monomers, the following definitions are proposed.

The term "alkyl group" is intended to mean, generally, in the above and in what follows, a linear or branched alkyl group containing from 1 to 20 carbon atoms or a cyclic alkyl group containing from 3 to 20 carbon atoms. By way of examples, mention may be made of methyl, ethyl, n-propyl, i-propyl, n-butyl, n-dodecanyl, i-butyl, t-butyl, cyclopropyl and cyclohexyl groups.

The term "aryl group" is intended to mean, generally, in the above and in what follows, an aryl group containing from 6 to 20 carbon atoms. By way of examples, mention may be made of benzyl, naphthyl and biphenyl groups.

The term "alkylaryl group" is intended to mean, generally, in the above and in what follows, an aryl group having the same definition as that given above, said group being substituted with at least one alkyl group having the same definition as that given above.

The term "—O-alkyl group" or "—O-aryl group" is intended to mean an alkyl group or an aryl group, corresponding to the same definition as that given above, the alkyl or aryl group being, in this case, linked to another part of the monomer by means of an oxygen atom.

The term "perfluoro group" is intended to mean a group in which all the hydrogen atoms are substituted by fluorine atoms.

When it is specified "it being possible for one or more oxygen, nitrogen, sulphur and/or selenium atoms to be intercalated in said groups" (i.e. alkyl, aryl, alkylaryl, —O-aryl and —O-alkyl groups), this means, in other words, that a carbon atom is replaced with an —O—, —S—, —N— or —Se— group.

The term "ethylenic group" is intended to mean a carbon-based group comprising two carbon atoms linked by a double bond, this group being capable of being polymerized by free-radical polymerization. A particular ethylenic group is a vinyl group $CH_2=CH-$, or an (alkyl)acrylate group, such as a (meth)acrylate group.

The term "acyl group" is intended to mean a —CO-alkyl group, the alkyl group corresponding to the same definition as that given above.

The term "salt" is intended to mean the compounds of ionic structure. For example, mention may be made of metal carboxylate salts, when R' corresponds to $OR_{13}$ with $R_{13}$ being a metal. In this situation, the term "metal" is conventionally intended to mean a monovalent metal, such as an alkali metal, for instance Na or K.

The term "metal element" is conventionally intended to mean an alkali metal, an alkaline-earth metal, a transition metal, a lanthanide, an actinide, and also the elements Al, Ga, Ge, In, Sn, Sb, Tl, Pb, Bi and Po.

In particular, the metal element is advantageously a lanthanide, such as ytterbium.

It is specified that the indices k, l and m represent the number of repeats of the unit given in parentheses, it being possible for this number to range from 0 to 20.

Particular monomers may be those for which R is a group of formula:

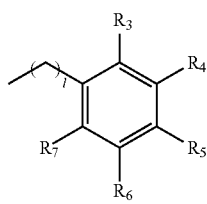

and at least one of $R^1$ and $R^2$ is a group of formula:

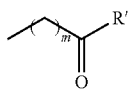

$R_3$ to $R_7$, R', l and m having the same meanings as those explained above, always with the proviso that at least one of $R_3$ to $R_7$ represents an ethylenic group.

More particularly, monomers in accordance with the definition given above are monomers for which R is a group of formula:

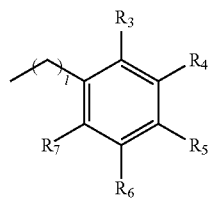

$R_1$ is a group of formula:

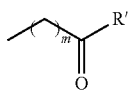

and $R_2$ is a hydrogen atom, l and m, $R_3$ to $R_7$ and R' having the same meanings as those given above, with the proviso that at least one of $R_3$ to $R_7$ represents an ethylenic group. In particular, l and m may be equal to 1.

A particular monomer of this type corresponds to formula (II) below:

(II)

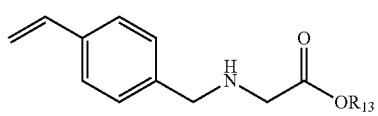

$R_{13}$ representing, in particular, H, a metal such as an alkali metal (for instance Na or K) or an alkyl group, such as an ethyl group.

Another group of monomers falling under the definition of the monomers of formula (I) corresponds to the monomers for which R is a group of formula:

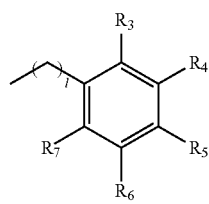

$R_1$ is a group of formula:

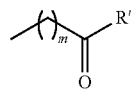

and $R_2$ is a group of formula:

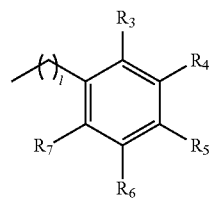

l and m, $R_3$ to $R_7$ and R' having the same meanings as those given above, with the proviso that at least one of $R_3$ to $R_7$ represents an ethylenic group. In particular, l and m may be equal to 1.

A particular monomer of this type corresponds to formula (III) below:

(III)

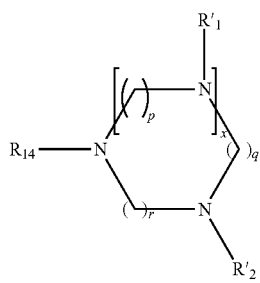

$R_{13}$ representing, in particular, H, a metal (such as an alkali metal, for instance Na or K) or an alkyl group, such as an ethyl group.

Other monomers that can be used, advantageously, in the process of the invention may be monomers comprising a cyclic amine containing at least two nitrogen atoms.

Particular monomers of this type correspond to formula (IV) below:

(IV)

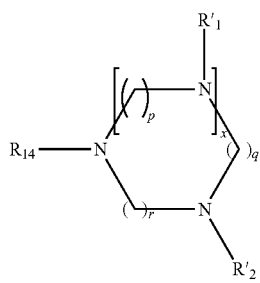

in which:
$R_{14}$ represents a group chosen from the groups of formulae below:

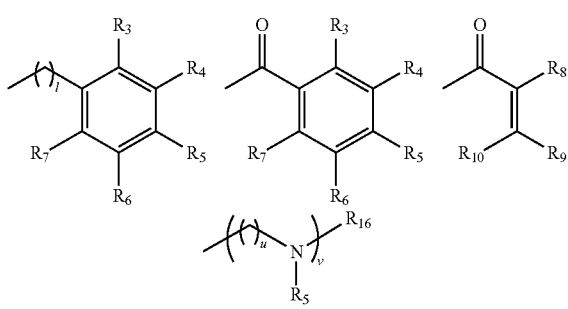

R'$_1$ and R'$_2$ represent, independently, an alkyl group, an aryl group, or a group having the formulae below:

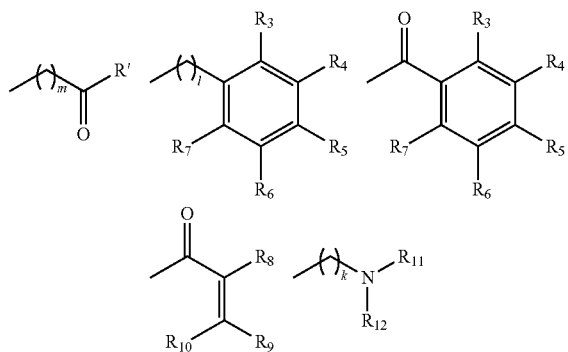

R$_{11}$ and R$_{12}$ corresponding, independently, to groups corresponding to the same definition as R'$_1$ and R'$_2$ given above;
R' is an OR$_{13}$ or amine group;
R$_3$, R$_4$, R$_5$, R$_6$ and R$_7$ represent, independently, H, an ethylenic group, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated in said groups, with the proviso that at least one of R$_3$, R$_4$, R$_5$, R$_6$ and R$_7$ represents an ethylenic group;
R$_8$, R$_9$ and R$_{10}$ represent, independently, H, an ethylenic group, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated in said groups;
R$_{15}$ represents a group having the formulae below:

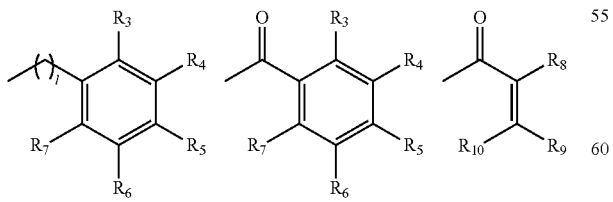

the R$_3$ to R$_{10}$ being as defined above;
R$_{13}$ represents H, a metal, an alkyl group, an aryl group, an acyl group, an alkylaryl group, said alkyl, aryl and alkylaryl groups being optionally perfluorinated, and it being possible for one or more oxygen, sulphur and/or selenium atoms to be intercalated in said groups;
R$_{16}$ represents a group of formula:

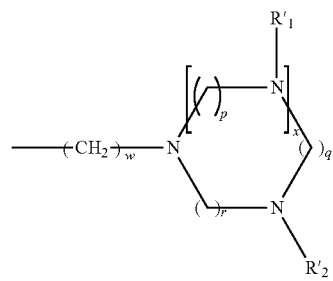

the R'$_1$ and R'$_2$ being as defined above;
k, l, m, u, p, q, r, x and w are integers ranging from 0 to 20, v is an integer ranging from 1 to 20, with the proviso that, when x is equal to 0, (r+q) is at least equal to 2, and when x is equal to 1, at least one of p, q and r is other than 0.

It is specified that p, q, r and x correspond to the number of repeats of the unit given between parentheses (for p, q and r) or between square brackets (for x).

Advantageously, valuable monomers are monomers for which R$_{14}$ represents a group of formula below:

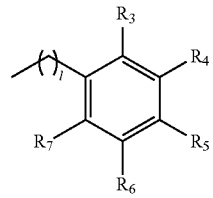

and at least one of R'$_1$ and R'$_2$ represents

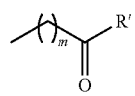

the R$_3$ to R$_7$, R', l and m corresponding to the same definition as that given above, p, q, r and x being advantageously at least equal to 1, always with the proviso that at least one of R$_3$ to R$_7$ represents an ethylenic group.

More particularly, monomers in accordance with the definition given above are monomers for which R$_{14}$ is a group of formula:

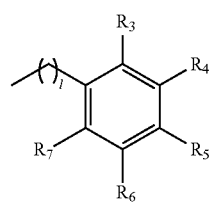

$R'_1$ and $R'_2$ represent a group of formula:

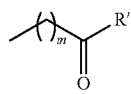

the $R_3$ to $R_7$, R', l and m corresponding to the same definition as that given above, p, q, r and x being advantageously at least equal to 1, always with the proviso that at least one of $R_3$ to $R_7$ represents an ethylenic group. In particular, l and m may be integers equal to 1, and p, q, r and x may be integers equal to 2.

A particular monomer corresponding to the definition above is a monomer corresponding to formula (V) below:

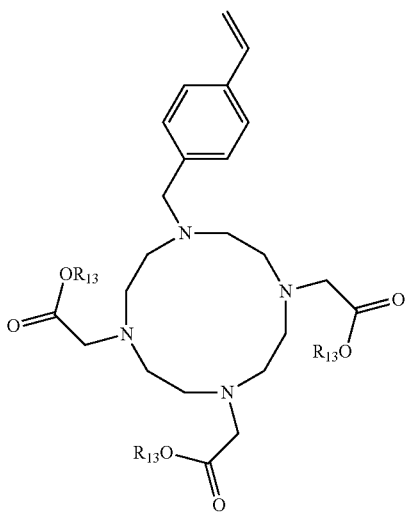

(V)

$R_{13}$ representing, in particular, H, an alkyl group, such as an ethyl group, or a metal.

Thus, for the monomer of formula (V), $R_{14}$ corresponds to a group of formula:

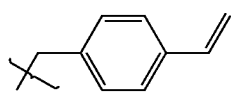

while $R_1$ and $R_2$ correspond to a group of formula —$CH_2$—$COOR_{13}$, and p, q, r and x are integers equal to 2.

Advantageously, $R_{14}$ may represent, also, a group of formula:

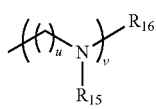

and at least one of $R'_1$ and $R'_2$ represents:

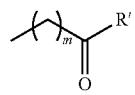

$R_{15}$, $R_{16}$, R', m, u and v corresponding to the same definitions as those given above, and p, q, r and x being advantageously at least equal to 1.

It is specified that, when $R_{14}$ corresponds to a group of formula:

the monomers can be represented by the general formula below:

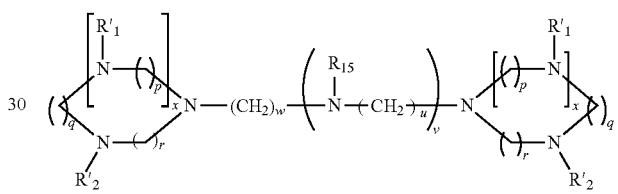

A group of particular monomers coming under the definition given above corresponds to those for which $R_{15}$ corresponds to a group of formula:

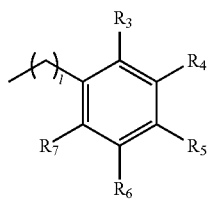

l and the $R_3$ to $R_7$ corresponding to the same definition as that given above, with the proviso that at least one of $R_3$ to $R_7$ represents an ethylenic group, and the groups $R'_1$ and $R'_2$ represent a group of formula:

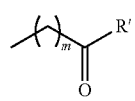

with m and R' corresponding to the same definitions as those given above, p, q, r and x being advantageously at least equal to 1. In particular, p, q, r, x, u, v and w represent, for example, an integer equal to 2.

A particular monomer coming under the definition above corresponds to formula (VI) below:

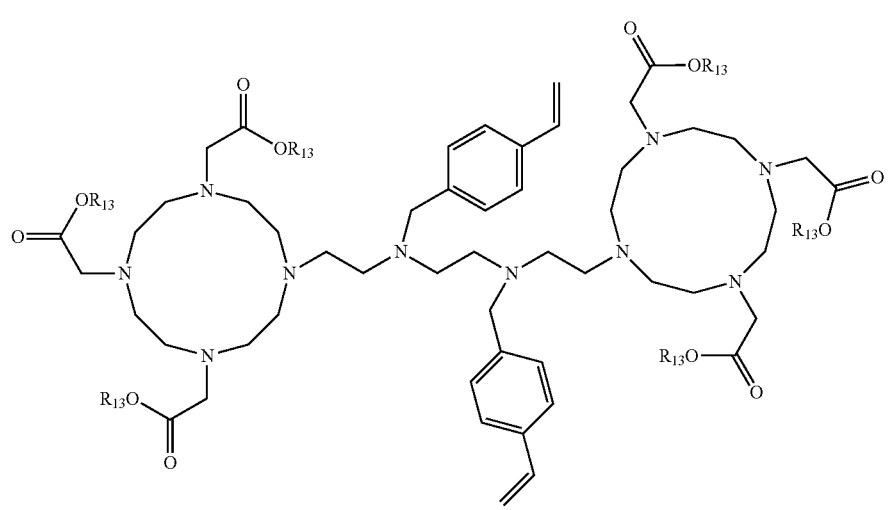
(VI)

$R_{13}$ representing, in particular, H, a metal, or an alkyl group, such as an ethyl group,
and the optional salts thereof.

Thus, for this monomer of formula (VI), the $R_{15}$ represent a group of formula:

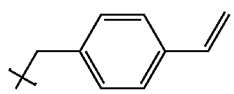

while $R'_1$ and $R'_2$ correspond to a group of formula —$CH_2$—$COOR_{13}$, and p, q, r, x, u, v and w are integers equal to 2.

By virtue of the presence of nitrogen atoms bearing free doublets, these monomers are capable of forming a coordination complex with the appropriate metal element.

The metal element may be an alkali metal, an alkaline-earth metal, a transition metal, a lanthanide, an actinide, and also the elements Al, Ga, Ge, In, Sn, Sb, Tl, Pb, Bi and Po.

In particular, the metal element is advantageously a lanthanide, such as ytterbium.

The formation of coordination complexes will be further explained below.

Thus, before the polymerization step, the process of the invention may comprise a step of preparing the abovementioned coordination complex. For example, the formation of the complex may consist in bringing the abovementioned monomers into contact with an aqueous and/or organic solution comprising the appropriate metal element.

Conventionally, the polymerization step of the process of the invention takes place, in addition to the presence of the coordination complex, in the presence, optionally, of a polymerization initiator and, optionally, of a porogenic solvent and of one or more comonomers.

Advantageously, when the polymerization step takes place without comonomers, the monomers which go to make up the coordination complexes will comprise at least two ethylenic groups.

The polymerization initiator is a free-radical initiator conventionally chosen from peroxide compounds, azonitrile compounds (such as 2,2'-azobisisobutyronitrile), azoester compounds and azoamide compounds.

The initiator may be introduced, into the polymerization medium, according to varying amounts, for example according to amounts that can range from 0 to 50% by mass, relative to the total mass of monomers used.

The porogenic solvent may be a polar or an apolar organic solvent and may be chosen from ether solvents (such as tetrahydrofuran), dimethyl sulphoxide, phthalate solvents (such as dimethyl phthalate or dibutyl phthalate), alcoholic solvents (such as methanol or ethanol), aromatic solvents (such as toluene or fluorobenzene), and ketone solvents.

The polymerization step may be carried out in the presence of one or more comonomers, said comonomers generally being different from the monomers that go to make up the coordination complexes.

These comonomers may be chosen from styrene monomers or acrylate monomers.

Advantageously, the comonomers comprise at least two ethylenic groups, thus playing the role of a crosslinking agent. The materials thus obtained exhibit good mechanical strength.

Comonomers that can be used may be styrene monomers of formula (VII) below:

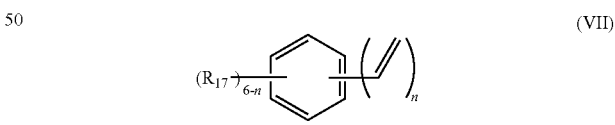
(VII)

in which the (6-n) $R_{17}$, which may be identical or different, represent a hydrogen atom, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, and n is an integer ranging from 1 to 3, preferably n being equal to 2.

In particular, an appropriate comonomer may be divinylbenzene, in particular 1,4-divinylbenzene.

Comonomers that can be used may also be acrylate compounds of formula (VIII) below:

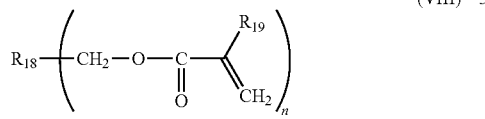

(VIII)

in which $R_{18}$ represents an alkyl group, $R_{19}$ represents H or an alkyl group, and n being an integer ranging from 1 to 3.

In particular, an appropriate comonomer of this type may be trimethylolpropanetriacrylate (known under the abbreviation TMPTA) of formula below:

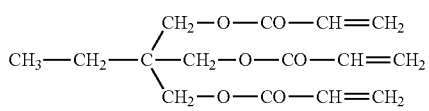

Conventionally, the polymerization step is carried out at a temperature ranging from 40 to 100° C.

In particular, the polymerization step may consist of:
the copolymerization of a coordination complex formed from a monomer of formula (V) and from ytterbium, in the presence of divinylbenzene;
the polymerization of a coordination complex formed from monomers of formula (II) and from ytterbium;
the copolymerization of a coordination complex formed from monomers of formula (II) and from ytterbium, in the presence of divinylbenzene or of trimethylolpropanetriacrylate;
the polymerization of a coordination complex formed from monomers of formula (III) and from copper.

After the polymerization step, a gel is obtained, corresponding to a three-dimensional network, the structure of which is impregnated with the solvent. The gel, once synthesized, must be dried, in order to obtain the dry doped polymeric material.

Thus, the process advantageously comprises a step of drying the gel obtained, this step being advantageously a supercritical $CO_2$ drying step. To do this, this supercritical $CO_2$ drying step can be preceded by a solvent exchange step consisting in replacing the solvent present in the pores of the gel with a $CO_2$-miscible solvent. This supercritical $CO_2$ drying step makes it possible in particular to respect the physical integrity of the foam.

By virtue of the process of the invention, polymeric materials doped with a metal element, having a high percentage of metal element (that can be greater than 20% by mass), and with a molecular-scale distribution of the metal element within the material, are obtained.

Thus, the invention relates to polymeric materials doped with at least one metal element, that can be obtained by means of a process as defined above.

These materials can be employed in many fields requiring the use of materials doped with metal elements, and in particular in the production of elements of laser targets used, in particular, in inertial confinement fusion experiments.

Particular materials in accordance with the invention are materials obtained by:
the copolymerization of a coordination complex formed from a monomer of formula (V) and from ytterbium, in the presence of divinylbenzene;
the polymerization of a coordination complex formed from monomers of formula (II) and from ytterbium;
the copolymerization of a coordination complex formed from monomers of formula (II) and from ytterbium, in the presence of divinylbenzene or of trimethylolpropanetriacrylate;
the polymerization of a coordination complex formed from monomers of formula (III) and from copper.

They can be used as a catalyst, or as luminescent or magnetic materials.

Finally, they can be used as ion-imprinted materials. To do this, the doped materials obtained by means of the process of the invention can be subjected to an acid treatment, intended to remove a part of the metal elements complexed in said material. The vacant sites thus constitute specific imprints of the specific element of the metal initially introduced. This treatment results in an "ion-imprinted" material capable of selectively trapping the "imprinted" metal element when brought into contact with a fluid comprising said metal element. Materials of this type can thus be used for the selective extraction of metals, in particular, during the reprocessing of nuclear fuel effluents, such as the separation of lanthanides, or else the decontamination of biological fluids.

Among the monomers that can be used in the context of the process of the invention, some are novel.

Thus, the invention also relates to novel monomers, these monomers corresponding to those of general formulae (I) and (IV) defined above and to those of particular formulae (II), (III), (V) and (VI) as defined above.

These monomers are conventionally produced by nucleophilic substitution reactions between amines and halogenated compounds.

Thus, by way of example, the preparation of the final monomer of formula (V), with $R_{13}$ corresponding to H or Na, can take place, for example, according to the following reaction scheme in three steps:
a first step 1) consisting of functionalization with an alkyl bromoacetate compound;
a second step 2) consisting of alkylation;
a third step 3) consisting of deprotection in an acidic or basic medium so as to free the carboxylic groups

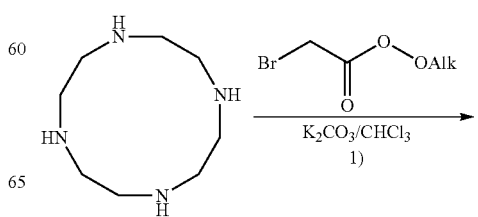

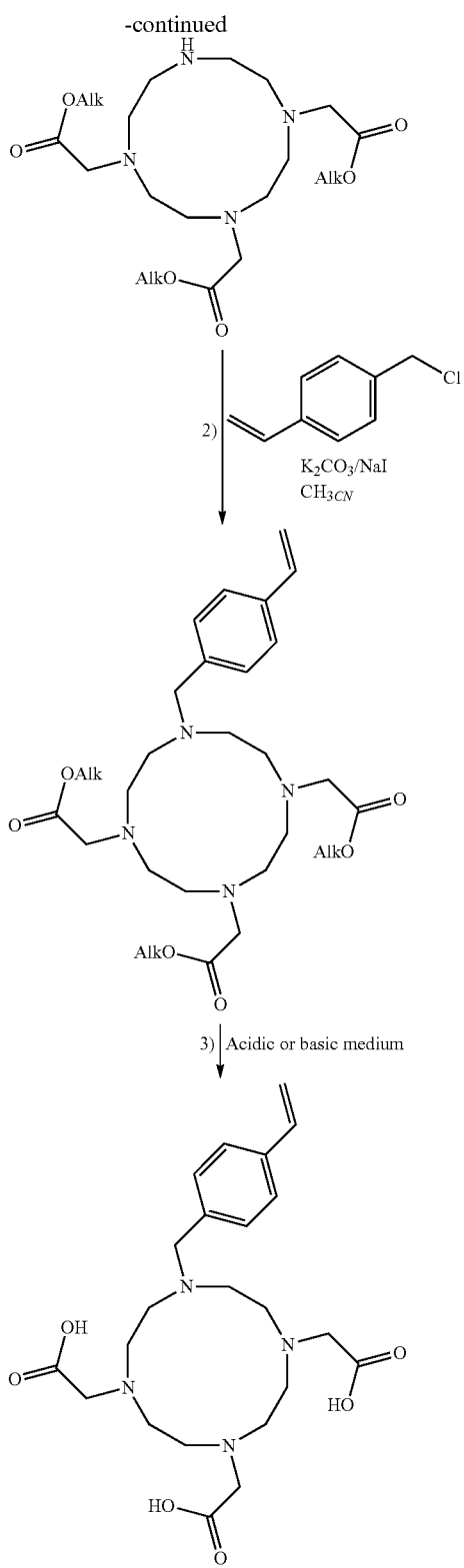

Alk corresponding to an alkyl group, such as a methyl, ethyl, propyl or butyl (in particular, t-butyl) group.

As previously mentioned, the monomers as defined above are used in the form of coordination complex with at least one metal element, in the process for preparing the polymeric materials of the invention.

Thus, the invention also relates to coordination complexes comprising at least one metal element and at least one monomer of formulae (I) to (VI) as defined above.

The metal element may be an alkali metal, an alkaline-earth metal, a transition metal, a lanthanide, an actinide, and also the elements Al, Ga, Ge, In, Sn, Sb, Tl, Pb, Bi and Po.

In particular, the metal element is advantageously a lanthanide, such as ytterbium.

The abovementioned coordination complexes are obtained by bringing the monomers of formulae (I) to (VI) as defined above, optionally in the form of salts, into contact with a compound of $MX_n$, M representing the metal element, X an anion and n the valence of said metal element.

By way of examples, X may be a chloride, bromide, fluoride, iodide, iodate, nitrate, sulphate, sulphonate, sulphite, nitrate, nitrite, phosphate, phosphite, cyanide, azide, hydroxyl, chlorate, perchlorate, acetate, trifluoromethanesulphonate (or triflate), trifluoroacetate, trichloroacetate, alkoxide, acetylacetonate, cyclopentadienyl or alkynide.

The reaction for formation of the complexes can be carried out in an aqueous or organic medium or in a multiphase emulsion.

Particular complexes are complexes of monomers of formula (II), (III) or (V) with a metal, element, such as ytterbium or copper.

The invention will now be described in more detail in relation to the examples given below, provided by way of nonlimiting illustration.

DETAILED DESCRIPTION OF PARTICULAR EMBODIMENTS

Example 1

This example illustrates the preparation of a monomer of formula below:

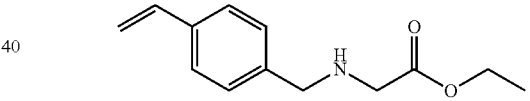

referred to as compound $Gly^2OEt$.

21.9 g of ethyl glycinate hydrochloride (3 eq., 157.2 mmol), 18.1 g of potassium carbonate (2.5 eq., 131.0 mmol) and 150 ml of anhydrous acetonitrile are charged to a 250 ml two-necked round-bottomed flask surmounted by a condenser, under an argon atmosphere. The mixture is stirred vigorously for 10 minutes at ambient temperature and 8 g of 4-vinylbenzene chloride (1 eq., 52.4 mmol) are added. The reaction medium is brought to 70° C. and stirred vigorously for 18 hours. The reaction medium is then allowed to return to ambient temperature and filtered in order to remove the salts. After evaporation of the filtrate under reduced pressure, 19.4 g of crude product are obtained in the form of a yellow-coloured viscous oil. The crude product is purified on silica gel neutralized with triethylamine (300 g of silica, eluent: 100% dichloromethane then 98/2 dichloromethane/methanol mixture). 11.3 g of product are isolated in the form of a pale yellow liquid.

Yield: 98%.

Physicochemical Characteristics $^1$H NMR (200.13 MHz, $CDCl_3$): $\delta_H$ 1.27 (3H, t,j=7.2 Hz, $CH_2CH_3$), 2.00 (1H, s, NH), 3.40 (2H, s, —$CH_2CO$—), 4.13 (2H, s, $CH_2Ar$.), 4.18 (2H, q,j=7.2/7.0 Hz, $CH_2CH_3$), 5.21 (1H, dd,j=0.7/10.8 Hz, CH=$CH_2$), 5.74 (1H, d,j=0.7/17.6

Hz, CH=CH$_2$), 6.70 (1H, dd,j=10.8/17.6 Hz, CH=CH$_2$.), 7.28 (2H, d,j=8.0 Hz, CH—Ar), 7.37 (2H, d,j=8.2 Hz, CH—Ar)

$^{13}$C NMR (50.32 MHz, CDCl$_3$): $\delta_c$ 13.8; 43.6; 52.5; 60.3; 113.0; 125.9 (2C); 128.0 (2C); 136.1; 136.2; 139.0; 173.9.

Example 2

This example illustrates the preparation of the monomer of formula below:

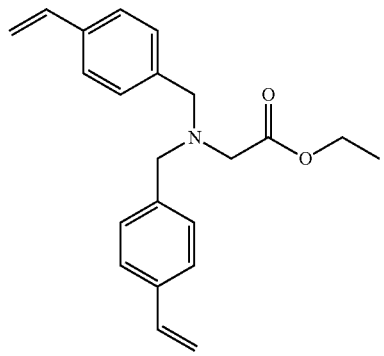 [SMILES: C=Cc1ccc(CN(CC(=O)OCC)Cc2ccc(C=C)cc2)cc1]

referred to as compound Gly$^2$'OEt.

1 g of ethyl glycinate hydrochloride (7.1 mmol), 3.37 g of potassium carbonate (1.7 eq., 12.2 mmol), 2.18 g of 4-vinylbenzyl chloride (2 eq., 14.3 mmol), 5 mol % of sodium iodide and 30 ml of anhydrous acetonitrile are charged to a 100 ml round-bottomed flask surmounted with a condenser, under an argon atmosphere. The mixture is brought to 70° C. and stirred for 16 hours. The reaction medium is then allowed to return to ambient temperature and filtered in order to remove the salts. The solvent is evaporated off under reduced pressure and the residue is taken up in 20 ml of ethyl ether. The salts, which have again precipitated, are removed by filtration. After evaporation of the filtrate under reduced pressure, 2.17 g of a 95% pure, yellow-coloured oil are obtained. Yield: 87%.

Physicochemical Characteristics $^1$H NMR (200.13 MHz, CDCl$_3$): $\delta_H$ 1.29 (3H, t,j=8.0 Hz, CH$_2$CH$_3$), 3.32 (2H, s, CH$_2$CO), (3.83 4H, s, CH$_2$Ar), 4.19 (2H, q,j=8.0/6.0 Hz, CH$_2$CH$_3$), 5.24 (2H, dd,j=0.8/12.0 Hz, CH=CH$_2$), 5.77 (2H, dd, j=0.8/18.0 Hz, CH=CH$_2$), 6.75 (2H, dd, j=10.8/17.6 Hz, CH=CH$_2$), 7.0-7.40 (8H, m, CH—Ar).

Example 3

This example illustrates the preparation of the monomer of formula below:

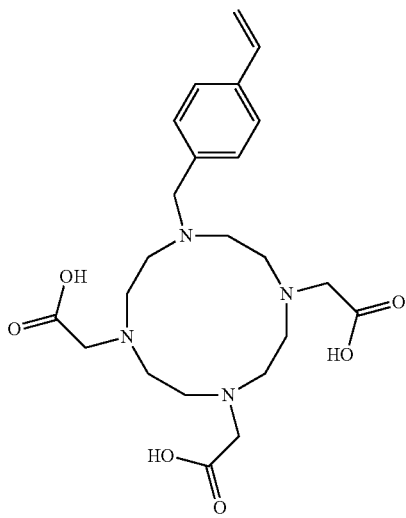 [SMILES: C=Cc1ccc(CN2CCN(CC(=O)O)CCN(CC(=O)O)CCN(CC(=O)O)CC2)cc1]

a) Stage 1: Synthesis of 1,4,7-tris(tert-butoxycarboxymethyl)-1,4,7,10-tetraazacyclododecane of formula below:

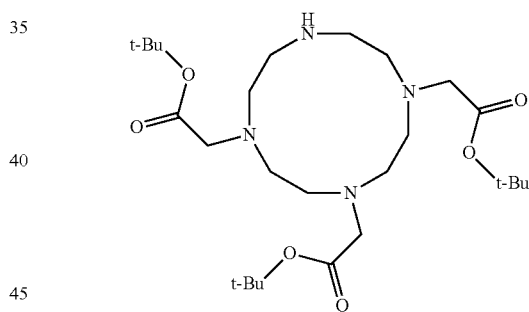

1 g of cyclene (5.8 mmol), 0.8 g of potassium carbonate (5.8 mmol, 1 eq.) and 150 ml of anhydrous chloroform are placed in a round-bottomed flask surmounted by a dropping funnel. The mixture is stirred vigorously and a solution of tert-butyl bromoacetate (3 eq., 3.39 g, 17.4 mmol) in 50 ml of anhydrous chloroform is added dropwise, over 4 hours. After addition is complete, the medium is stirred at ambient temperature for 72 hours. The reaction medium is then filtered in order to remove the salts, and the filtrate is evaporated. The residue is solubilized in 10 ml of toluene under hot conditions, and then the solution is allowed to return to ambient temperature. The solid which is crystallized is recovered by filtration, washed with 10 ml of toluene and dried under reduced pressure. 2.50 g of 1,4,7-tris(tert-butoxycarboxymethyl)-1,4,7,10-tetraazacyclodecane are isolated in the form of a white powder. Yield=82%.

Physicochemical Characteristics $^1$H NMR (200.13 MHz, CDCl$_3$): δ$_H$ 1.43 (18H, s, tert-Bu), 1.48 (9H, s, tert-Bu), 2.89-3.08 (16H, m, —CH$_2$—CH$_2$N—), 3:28 (2H, s, —CH$_2$CO$_2$—), 3.36 (4H, s, —CH$_2$CO$_2$—), 9.94 (1H, m, NH).

b) Stage two: Synthesis of N-{5-[4,7,10-tris(tert-butoxycarbonylmethyl)-1,4,7,10-tetraazacyclododecan-1-yl]methyl}styrene of formula below:

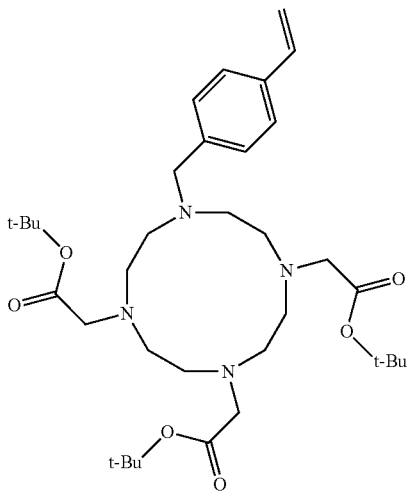 [SMILES: C=Cc1ccc(CN2CCN(CC(=O)OC(C)(C)C)CCN(CC(=O)OC(C)(C)C)CCN(CC(=O)OC(C)(C)C)CC2)cc1]

2.40 g of 1,4,7-tris(tert-butoxycarboxy-methyl)-1,4,7,10-tetraazacyclododecane (4.67 mmol), 1.1 g of 4-vinylbenzyl chloride (1.5 eq., 7.00 mmol), 0.97 g of potassium carbonate (1.5 eq., 7 mmol), 0.7 g of sodium iodide (1 eq., 4.67 mmol) and 70 ml of anhydrous acetonitrile are charged to a two-necked round-bottomed flask surmounted by a condenser and under an argon atmosphere. The reaction medium is stirred and brought to the temperature of 70° C. for 20 hours. The medium is then allowed to return to ambient temperature, and filtered, and the filtrate is evaporated under reduced pressure. The oil obtained is taken up in 100 ml of diethyl ether and the mixture is left for 1 hour. The solid, which has precipitated, is recovered by filtration, washed with twice 30 ml of diethyl ether and dried under vacuum. 2.46 g of N-{5-[4,7,10-tris(tert-butoxycarbonylmethyl)-1,4,7,10-tetraazacyclodecan-1-yl]methyl}styrene are obtained in the form of a white powder. Yield: 84%.

Physicochemical Characteristics $^1$H NMR (200.13 MHz, CDCl$_3$): δ$_H$ 1.46 (27H, s, tert-Bu), 2.10-2.52 (16H, m, —CH$_2$—CH$_2$N), 2.81 (6H, m, —CH$_2$CO$_2$—) 3.02 (2H, s, CH$_2$Ar), 5.24 (1H, d, j=10.6 Hz, CH$_2$=CH), 5.70 (1H, d,j=18 Hz, CH$_2$=CH), 6.64 (1H, dd, J=11/18 Hz, CH=CH$_2$), 7.29 (2H, d, j=9.2 Hz, CHAr), 7.38 (2H, d,j=9.9 Hz, CH—Ar)

$^{13}$C NMR (50.32 MHz, CDCl$_3$): δ$_c$ 27.4; 27.5; 49.4 (m.); 55.2; 55.4; 58.8; 81.9; 82.4; 113.8; 126.0; 129.8; 135.6; 136.3; 136.7; 172.0; 173.9 (2C).

MALDI-TOF: MH$^+$=631.443; MNa$^+$=653.425 (theoretical values: 631.443 and 653.425).

c) Stage 3: Synthesis of N-{5-[4,7,10-tris(acetic acid)-1,4,7,10-tetraazacyclododecan-1-yl]methyl}styrene (referred to as compound L1) of formula below:

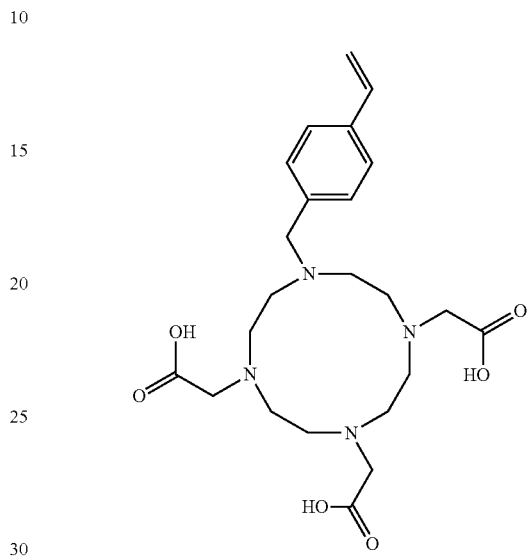

A solution of 10 ml of trifluoroacetic acid in 40 ml of dichloromethane is added, dropwise, to a solution of N-{5-[4,7,10-tris(tert-butoxycarbonyl-methyl)-1,4,7,10-tetraaza-cyclododecan-1-yl]methyl}styrene (2.0 g, 3.17 mmol) in 40 ml of dichloromethane, cooled in an ice bath. The reaction medium is stirred for 16 hours at ambient temperature and then the solvent is evaporated off under reduced pressure. The residual trifluoroacetic acid is coevaporated using ethanol. The semi-solid residue obtained is dissolved in 15 ml of anhydrous acetone and flocculated in 250 ml of anhydrous ethyl ether. The supernatant is removed and, after the precipitate has been dried under vacuum, 1.36 g of N-{5-[4,7,10-tris(acetic acid)-1,4,7,10-tetraazacyclodecan-1-yl]methyl}styrene are isolated in the form of a yellow powder with a yield of 93%.

Physicochemical Characteristics $^1$H NMR (200.13 MHz, DMSO-d$_6$): δ$_H$ 2.60-3.43 (24H, m, CH$_2$), 4.21 (3H, m, COOH), 5.26 (1H, m, CH$_2$=CH), 5.79 (1H, m, CH$_2$=CH), 6.71 (1H, m, CH=CH$_2$), 7.0-7.47 (4H, m, CH Ar)

$^{13}$C NMR (50.32 MHz, DMSO-d$_6$): δ$_c$ 48.6 (m); 55.8 (m); 81.2; 81.8; 115.6; 125.8; 126.6; 130.5; 135.9; 138.0; 170.0; 172.0.

FAB$^+$ mass spectrometry MH$^+$=463; MNa$^+$=485 (theoretical values: 463 and 485).

Example 4

This example illustrates the synthesis of an N-{5-[4,7,10-tris(acetate)-1,4,7,10-tetraazacyclo-decan-1-yl]methyl}styrene ytterbium complex of formula below:

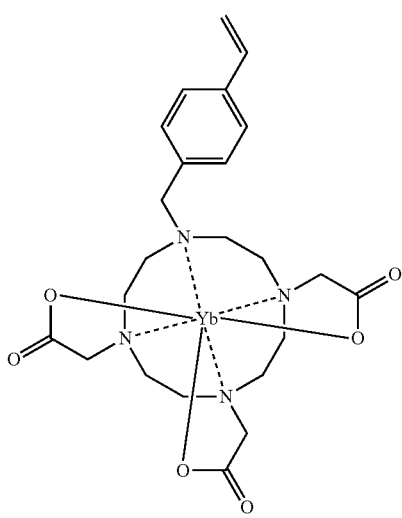

referred to as $C_1$-Yb complex.

A solution of $L^1$ (1.12 g, 2.42 mmol) in 40 ml of Milli Q quality water (Millipore) is adjusted to pH=7 with a 0.2 M solution of potassium hydroxide. The solution is filtered and a solution of ytterbium chloride (0.787 g, 2 mmol) in 30 ml of Milli Q water is added to the filtrate, with stirring and dropwise. The pH of the medium is adjusted to 6 at the end of the addition. After stirring for 1 h 30 at ambient temperature, the pH is again adjusted to 6 and then the solution is filtered. The filtrate is recovered and evaporated under reduced pressure. The residual solid is taken up in 80 ml of methanol and the salts which precipitate are removed by filtration. The operation is repeated until precipitates no longer form in the methanol. 1.11 g of $L^1$-Yb are isolated in the form of a white powder with a yield of 88%.

Physicochemical Characteristics $^1$H NMR (400.13 MHz, CD$_3$OD): $\delta_H$ −136.0; −94.0; −89.7; −82.4; −74.0; −71.6; −56.2; −54.9; −33.8; −26.7; −12.6; 23.0; 24.5; 38.2; 40.4; 45.7; 65.3; 143.8; 161.9; 186.9; 210.6

MALDI-TOF: MH$^+$=634.48 and MNa$^+$=656.14 (Theoretical values: 634.17 and 656.15).

Example 5

This example illustrates the preparation of the salt of formula below:

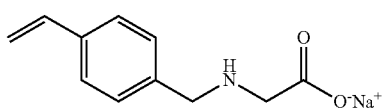

4.67 ml of sodium hydroxide at the concentration of 35% by mass are added to a solution of Gly$^2$OEt (11.3 g) in 133 ml of anhydrous ethanol. The reaction medium is stirred for 16 hours at ambient temperature. The precipitate formed is isolated by filtration and rinsed with 20 ml of anhydrous ethanol. The filtrate is evaporated under reduced pressure and taken up in 30 ml of anhydrous ethanol. The white solid which precipitates is recovered by filtration. The two fractions are combined and, after drying under reduced pressure, 7.27 g of Gly$^2$Na are isolated in the form of a white powder. Yield: 66%.

Physicochemical Characteristics $^1$H NMR (200.13 MHz, D$_2$O): $\delta_H$ 3.14 (2H, s, —CH$_2$CO—), 3.69 (2H, s, CH$_2$Ar), 5.27 (1H, dd, j=0.8/11.8 Hz, CH$_2$=CH), 5.82 (1H, d, j=0.8/17.8 Hz, CH$_2$=CH), 6.76 (1H, dd, j=10.8/17.8 Hz, CH$_2$=CH), 7.32 (2H, d,j=8.2 Hz, CHAr), 7.47 (2H, d,j=8.2 Hz, CHAr)

$^{13}$C NMR (50.32 MHz, D$_2$O): $\delta_c$ 43.9; 51.2; 113.6; 125.8 (2C); 128.4 (2C); 135.8; 135.9; 138.0; 180.5.

Example 6

This example illustrates the preparation of the salt of formula below:

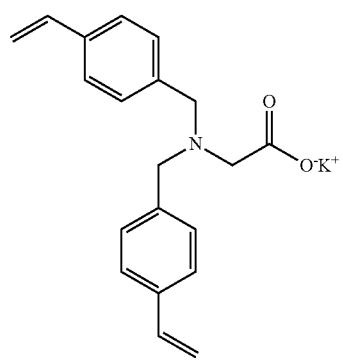

0.21 g of potassium hydroxide (1.25 eq., 3.7 mmol) is added to a solution of Gly$^{2'}$ OEt (1.00 g, 2.9 mmol) in 10 ml of an ethanol/distilled water solution (90/10). The reaction medium is stirred for hours at ambient temperature. The solvents are then evaporated off under reduced pressure and the residue is triturated from 8 ml of ethyl ether. The precipitate formed is isolated by filtration and 0.48 g of Gly$^{2'}$ K is isolated in the form of a pure white powder. Yield: 47%.

Physicochemical Characteristics $^1$H NMR (200.13 MHz, D$_2$O): $\delta_H$ 2.96 (2H, s, —CH$_2$CO—), 3.14 (4H, s, CH$_2$Ar), 4.98 (2H, d,j=12.0 Hz, CH$_2$=CH), 5.52 (2H, d,j 18.0 Hz, CH$_2$=CH), 6.47 (2H, dd,j=10.0/18.0 Hz, CH$_2$=CH), 7.14 (4H, d,j=8.0 Hz, CHM), 7.28 (4H, d,j=8.0 Hz, CHAr).

Example 7

This example illustrates the synthesis of a (Gly$^2$)$_x$Yb complex by reacting (Gly$^2$)Na with ytterbium triflate.

Gly$^2$Na (7.27 g, 3 eq., 34.09 mmol) in solution in 100 ml of distilled water is added, dropwise, to a solution of ytterbium triflate (7.05 g, 11.4 mmol) in 100 ml of distilled water, with vigorous stirring. After the addition of Gly$^2$Na is complete, the pH of the reaction medium is adjusted to 7.5 (using 1N sodium hydroxide or 1N hydrochloric acid) and the reaction medium is brought to 50° C. for 30 minutes. Once the reaction medium has returned to ambient temperature, the pH is again adjusted to 7.5 and the medium is stirred for 90 minutes. The precipitate formed is isolated by filtration, rinsed with 20 ml of distilled water and oven-dried for 6 hours (40° C., under vacuum). 5.46 g of a mixture of ytterbium complexes are obtained in the form of a white powder.

Physicochemical Characteristics of the White Powder Isolated

MALDI-TOF spectrum: 869; 891; 1015; 1038; 1285 and 1658.

This MALDI-TOF analysis (reproduced several times) shows that the powder is constituted of a mixture of various dinuclear ytterbium complexes which can by assumption correspond to the following general formula: $Yb_2(Gly^2)_x(OH)_y(H_2O)_z$ with x, y and z being variables.

For example: if x=3, y=3 and z=4, $MH^+$=1038.

If x=2, y=4 and z=4, $MH^+$=869.

Yb elemental analysis: Observed % by mass of Yb=30.6%+1.2% (mean value).

Example 8

This example illustrates the synthesis of a complex formed from carboxylate salts of monomers of formula (III) and of copper (referred to as $(Gly^2)_2Cu$ complex).

The compound $Gly^{2'}K$ (0.92 g, 2 eq., 2.7 mmol) in solution in 10 ml of distilled water is added, dropwise, to a solution of copper(II) chloride (0.18 g, 1.3 mmol) also in 10 ml of distilled water. After the addition of $Gly^{2'}K$ is complete, the pH of the reaction medium is adjusted to 10 with a 1N solution of sodium hydroxide. The reaction medium is stirred at ambient temperature for 3 hours. The precipitate formed is recovered by filtration, and the cake is washed with twice 20 ml of distilled water and dried at 50° C. under reduced pressure for 8 hours. 0.59 g of a purple-coloured powder is obtained. Yield=65%.

Physicochemical Characteristics

Cu elemental analysis: Theoretical % by mass of Cu=9.4%±0.4%

Observed % by mass of Cu=9.5%±0.4%.

Example 9

This example describes the preparation of an ytterbium-doped material obtained by copolymerization of $C^1$-Yb with divinylbenzene (DVB).

To do this, 1 ml of DMSO, 100 mg of comonomers ($C^1$-Yb+DVB with variable ratios) and 10 mg of AiBN are charged to a 10 ml round-bottomed flask. The solution obtained is degassed by bubbling with argon for 5 min. Finally, the solution is transferred into a cylindrical glass mould using a syringe and brought to 75° C. for 24 hours. The gel obtained is immersed in ethanol for one week in order to exchange the DMSO with ethanol. The gel is then dried with supercritical $CO_2$, giving an ytterbium-doped foam. The degree of ytterbium is determined by elemental analysis.

Various tests were carried out with varying ratios between $C^1$-Yb/DVB and the following values were obtained:

| Theoretical % by mass Yb initial mixture* | 0.9 | 3.6 | 6.3 | 13.3 |
|---|---|---|---|---|
| Observed % by mass Yb in foams** | 0.56 ± 0.04% | 2.6 ± 0.1% | 5.1 ± 0.2% | 12.1 ± 0.5% |

*"Theoretical % by mass Yb" = % by mass of ytterbium in initial mixture of monomers (before polymerization),
**"Observed % by mass Yb" = observed % by mass of ytterbium in the foams isolated.

Example 10

This example illustrates the preparation of an ytterbium-doped material by polymerization of $(Gly^2)_xYb$ or copolymerization of $(Gly^2)_xYb/DVB$ (50/50) or $(Gly^2)_xYb/TMPTA$ (50/50).

To do this, 200 mg of $(Gly^2)_xYb$ alone, of $(Gly^2)_xYb/DVB$ (50/50) or of $(Gly^2)_xYb/TMPTA$ (50/50), 30 mg of AiBN, 3 ml of dibutyl phthalate, 3 ml of chloroform or of THF and 1 ml of methanol are charged to a 25 ml round-bottomed flask. The mixture is stirred at ambient temperature until a clear solution is obtained. The solution is then placed in a rotary evaporator in order to remove the chloroform and the methanol (bath temperature=35° C., approximately 15 minutes, final pressure=5 millibar). After the cosolvents have been evaporated off, 100 mg of comonomer are then added and the solution obtained is degassed by bubbling with argon for 5 minutes. Finally, the solution is transferred into a cylindrical glass mould using a syringe and brought to 90° C. for 16 hours.

The gel obtained is immersed in ethanol for one week in order to exchange the dibutyl phthalate with ethanol. The gel is then dried with supercritical $CO_2$, giving an ytterbium-doped foam. The degree of ytterbium is determined by elemental analysis.

Various tests were carried out and the following values were obtained:

|  | $(Gly^2)_xYb$ | $(Gly^2)_xYb/DVB$ | $(Gly^2)_xYb/TMPTA$ |
|---|---|---|---|
| Theoretical % by mass Yb initial mixture * | 30.6 | 22.6 | 21.3 |
| Observed % by mass Yb in foams ** | 30.8 ± 1.2 | 22.7 ± 0.9 | 21.4 ± 0.9 |

* "Theoretical % by mass Yb" = % by mass of ytterbium in initial mixture of monomers (before polymerization),
** "Observed % by mass Yb" = observed % by mass of ytterbium in the foams isolated.

Example 11

This example illustrates the preparation of a copper-doped material by polymerization of $(Gly^2)_2Cu$.

To do this, 1 ml of DMSO, 100 mg of $Gly^2Cu$ and 10 mg of AiBN are charged to a 10 ml round-bottomed flask. The solution obtained is degassed by bubbling with argon for 5 minutes and then transferred into a cylindrical glass mould using a syringe. The reaction medium is brought to 90° C. for 24 hours. The gel obtained is immersed in ethanol for one week in order to exchange the DMSO with ethanol. The gel is then dried with supercritical $CO_2$, giving a copper-doped, blue-coloured foam. The degree of copper is determined by elemental analysis.

Various tests were carried out and the following values were obtained:

Theoretical % by mass of Cu=9.4%,

Observed % by mass of Cu=7.2%±0.2%.

The invention claimed is:

1. A process for preparing a polymeric material doped with at least one metal element, comprising:

a step of polymerization of a coordination complex of said metal element which is formed from said metal element and from one or more ligands of said metal element, each said ligand belonging to at least one monomer comprising at least one ethylenic group, said monomer corresponding to formula (I):

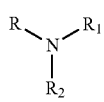
(I)

in which:
R represents a group chosen from the groups of formulae below:

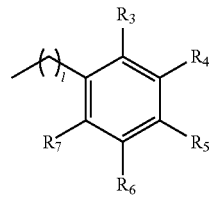 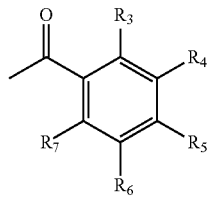 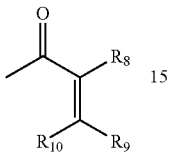

$R_1$ and $R_2$ represent, independently, H, an alkyl group, an aryl group, a group having the formulae below:

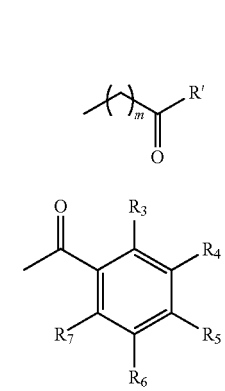 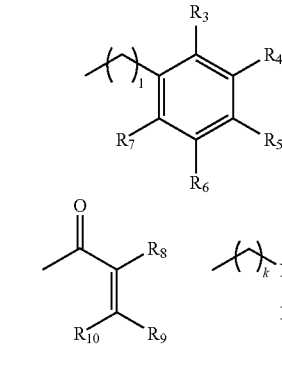 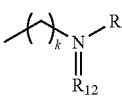

$R_{11}$ and $R_{12}$ corresponding, independently, to groups corresponding to the same definition as $R_1$ and $R_2$ given above;
R' is an $OR_{13}$ or amine group;
$R_3$, $R_4$, $R_5$, $R_6$ and $R_7$ represent, independently, H, an ethylenic group, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated into said groups, with the proviso that at least one of $R_3$, $R_4$, $R_5$, $R_6$ and $R_7$ represents an ethylenic group;
$R_8$, $R_9$ and $R_{10}$ represent, independently, H, an ethylenic group, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated in said groups;
$R_{13}$ represents H, a metal, an alkyl group, an aryl group, an acyl group or an alkylaryl group, said alkyl, aryl and alkylaryl groups being optionally perfluorinated, and it being possible for one or more oxygen, sulphur and/or selenium atoms to be intercalated in said groups;
k, l and m are integers ranging from 0 to 20;
and the salts thereof, or corresponding to formula (IV) below:

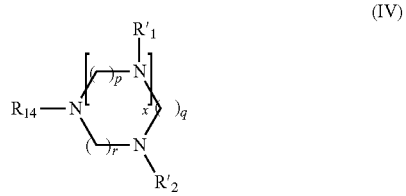
(IV)

in which:
$R_{14}$ represents a group chosen from the groups of formulae below:

$R'_1$ and $R'_2$ represent, independently, an alkyl group, an aryl group, or a group having the formulae below:

$R_{11}$ and $R_{12}$ corresponding, independently, to groups corresponding to the same definition as $R'_1$ and $R'_2$ given above;
R' is an $OR_{13}$ or amine group;
$R_3$, $R_4$, $R_5$, $R_6$ and $R_7$ represent, independently, H, an ethylenic group, an alkyl group, an aryl group, an
—O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated in said groups, with the proviso that at least one of $R_3$, $R_4$, $R_5$, $R_6$ and $R_7$ represents an ethylenic group;
$R_8$, $R_9$ and $R_{10}$ represent, independently, H, an ethylenic group, an alkyl group, an aryl group, an
—O-aryl group, an —O-alkyl group, an acyl group, an alkylaryl group, a halogen atom, said alkyl, aryl, alkylaryl, —O-aryl and —O-alkyl groups being optionally perfluorinated, it being possible for one or more oxygen, nitrogen, sulphur and/or selenium atoms to be intercalated in said groups;

$R_{15}$ represents a group having the formulae below:

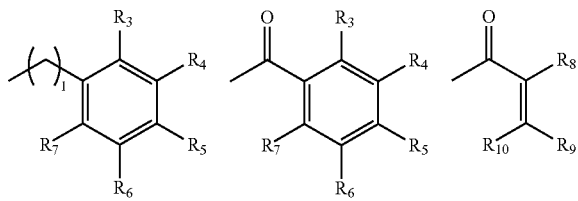

the $R_3$ to $R_{10}$ being as defined above;

$R_{13}$ represents H, a metal, an alkyl group, an aryl group, an acyl group, an alkylaryl group, said alkyl, aryl and alkylaryl groups being optionally perfluorinated, and it being possible for one or more oxygen, sulphur and/or selenium atoms to be intercalated in said groups;

$R_{16}$ represents a group of formula:

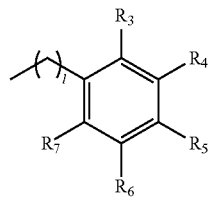

the $R'_1$ and $R'_2$ being as defined above; and k, l, m, u, p, q, r, x and w are integers ranging from 0 to 20, v is an integer ranging from 1 to 20, with the proviso that, when x is equal to 0, (r+q) is at least equal to 2, and when x is equal to 1, at least one of p, q and r is other than 0.

2. The process according to claim 1, in which R is a group of formula:

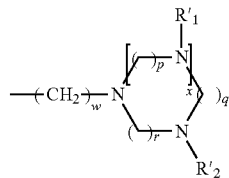

and at least one of $R_1$ and $R_2$ is a group of formula:

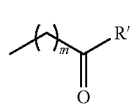

$R_3$ $R_7$, R', l and m having the same meanings as those disclosed in claim 1.

3. The process according to claim 1, in which R is a group of formula:

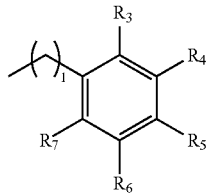

$R_1$ is a group of formula:

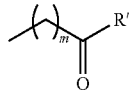

and $R_2$ is a hydrogen atom, $R_3$ to $R_7$, R', l and m having the same meanings as those disclosed in claim 1.

4. The process according to claim 3, in which the monomer corresponds to formula (II) below:

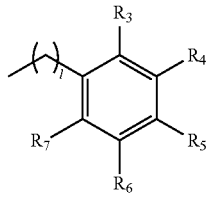

(II)

$R_{13}$ representing H, a metal or an alkyl group.

5. The process according to claim 1, in which R is a group of formula:

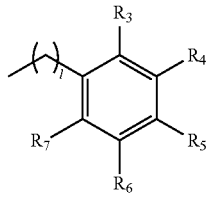

$R_1$ is a group of formula:

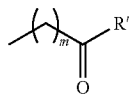

and $R_2$ is a group of formula:

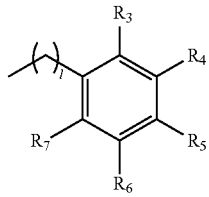

l and m, $R_3$ to $R_7$ and R' having the same meanings as those given in claim 1.

6. The process according to claim 5, in which the monomer corresponds to formula (III) below:

(III)

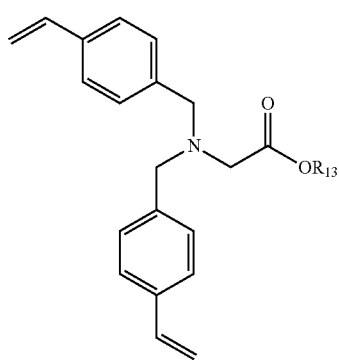

$R_{13}$ representing H, a metal or an alkyl group.

7. The process according to claim 1, in which $R_{14}$ represents a group of formula below:

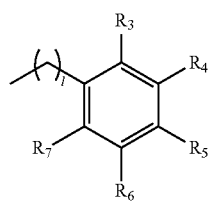

and at least one $R'_1$ and $R'_2$ represents:

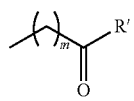

the $R_3$ to $R_7$, R', l and m corresponding to the same definition as that given in claim 1, p, q, r and x being at least equal to 1.

8. The process according to claim 1, in which $R_{14}$ is a group of formula:

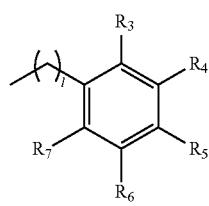

$R'_1$ and $R'_2$ represent a group of formula:

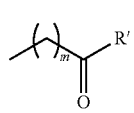

the $R_3$ to $R_7$, R', l and m corresponding to the same definition as that given in claim 1, p, q, r and x being at least equal to 1.

9. The process according to claim 1, in which the monomer corresponds to formula (V) below:

(V)

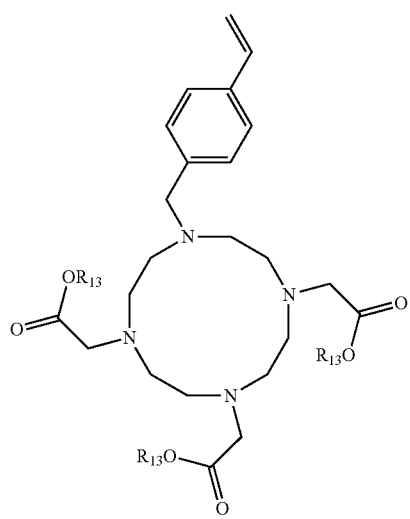

$R_{13}$ representing H, a metal or an alkyl group.

10. The process according to claim 1, in which $R_{14}$ represents a group of formula:

and at least one of $R'_1$ and $R'_2$ represents:

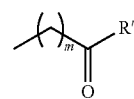

$R_{15}$, $R_{16}$, R', m, u and v corresponding to the same definitions as those given in claim 1, p, q, r and x being at least equal to 1.

11. The process according to claim 10, in which $R_{15}$ corresponds to a group of formula:

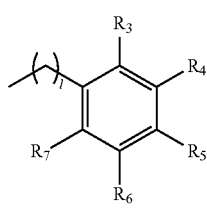

l, $R_3$ to $R_7$ corresponding to the same definition as that given in claim 1, and the groups $R'_1$ and $R'_2$ represent a group of formula:

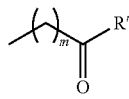

with m and R' corresponding to the same definition as that given in claim 1, p, q, r and x being at least equal to 1.

12. The process according to claim 11, in which the monomer corresponds to formula (VI) below:

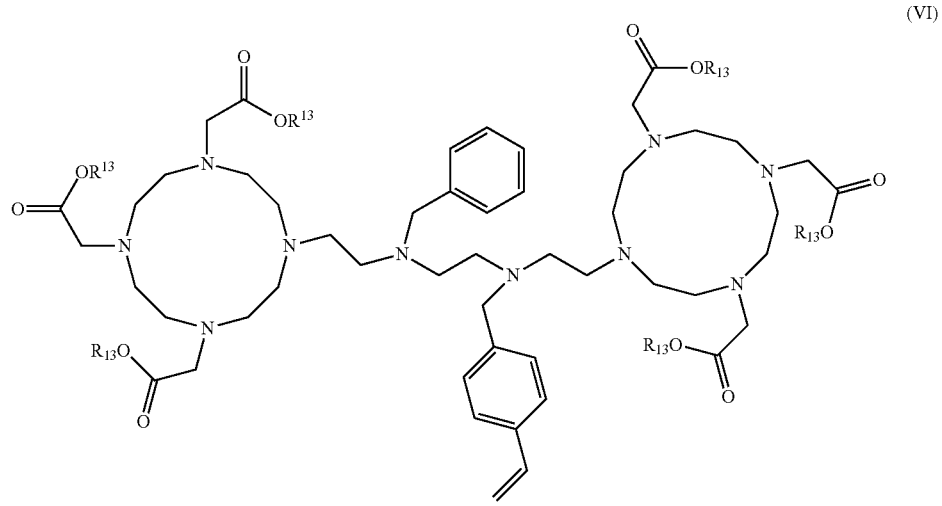

$R_{13}$ representing H, a metal or an alkyl group.

13. The process according to claim 1, in which the metal element is chosen from alkali metals, alkaline-earth metals, transition metals, lanthanides, actinides, and also the elements Al, Ga, Ge, In, Sn, Sb, Tl, Pb, Bi or Po.

14. The process according to claim 13, in which the metal element is a lanthanide element.

15. The process according to claim 1, in which the polymerization step is carried out in the presence of one or more comonomers different from the monomer defined according to claim 1.

16. The process according to claim 15, in which the comonomer(s) is (are) chosen from styrene monomers and acrylate monomers.

17. The process according to claim 15, in which the comonomer(s) comprise(s) at least two ethylenic groups.

18. The process according to claim 16, in which the comonomer(s) correspond(s) to either of formulae (VII) and (VIII) below:

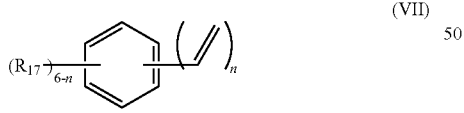

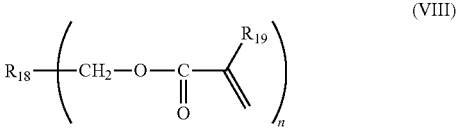

in which the (6-n) $R_{17}$, which may be identical or different, represent a hydrogen atom, an alkyl group, an aryl group, an —O-aryl group, an —O-alkyl group, an acyl group, an alkylaryl group, a halogen atom, said alkyl, aryl, alkylaryl, —O-aryl and —O-alkyl groups being optionally perfluorinated, $R_{18}$ represents an alkyl group, $R_{19}$ represents H or an alkyl group, and n being an integer ranging from 1 to 3.

19. The process according to claim 18, in which the comonomer is divinylbenzene.

20. The process according to claim 18, in which the comonomer is trimethylolpropanetriacrylate of formula below:

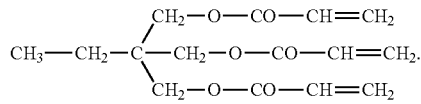

21. The process according to claim 1, comprising, before the polymerization step, a step of preparing the coordination complex as defined in claim 1.

22. The process according to claim 1, comprising, after the polymerization step, a supercritical $CO_2$ drying step.

23. The process according to claim 1, in which the polymerization step consists of:
copolymerization of a coordination complex formed from a monomer of formula (V) as defined in claim 9 and from ytterbium, in the presence of divinylbenzene;
polymerization of a coordination complex formed from monomers of formula (II) as defined in claim 4 and from ytterbium;
copolymerization of a coordination complex formed from monomers of formula (II) as defined in claim 4 and from ytterbium, in the presence of divinylbenzene or of trimethylolpropanetriacrylate; and
polymerization of a coordination complex formed from monomers of formula (III) as defined in claim 6 and from copper.

24. The polymeric material doped with at least one metal element that can be obtained by means of a process as defined according to claim 1.

25. The polymeric material as defined in claim 24, wherein said polymeric material is a catalyst, luminescent or magnetic materials, or ion-imprinted materials.

26. The polymeric material as defined in claim 24, wherein said polymeric material is an element of laser targets.

27. The process according to claim 14, in which the lanthanide element is ytterbium.

* * * * *